United States Patent [19]
Hrib et al.

[11] Patent Number: 5,801,176
[45] Date of Patent: Sep. 1, 1998

[54] SUBSTITUTED BENZOTHIENYLPIPERAZINES AND THEIR USE

[75] Inventors: Nicholas Joseph Hrib, Somerville, N.J.; John Gerard Jurcak, Bethlehem, Pa.; Abdul E. Mutlib, Bedminster, N.J.

[73] Assignee: Hoechst Marion Roussel, Inc.

[21] Appl. No.: 870,988

[22] Filed: Jun. 6, 1997

Related U.S. Application Data

[63] Continuation of Ser. No. 413,818, Mar. 17, 1995, abandoned.

[51] Int. Cl.[6] .................... A61K 31/495; C07D 405/04
[52] U.S. Cl. .................... 514/254; 544/362; 544/363; 544/373; 544/376
[58] Field of Search .................... 544/376, 373, 544/302, 363; 514/254

[56] References Cited

U.S. PATENT DOCUMENTS

| | | | |
|---|---|---|---|
| 4,968,792 | 11/1990 | Stack et al. | 540/524 |
| 5,240,927 | 8/1993 | Hrib et al. | 514/254 |
| 5,395,835 | 3/1995 | Glase et al. | 514/254 |
| 5,614,524 | 3/1997 | Matassa et al. | 514/253 |
| 5,639,764 | 6/1997 | Glamkowski et al. | 514/321 |

FOREIGN PATENT DOCUMENTS

| | | | |
|---|---|---|---|
| 138280 | 4/1985 | European Pat. Off. | 544/376 |
| 0316723 | 5/1989 | European Pat. Off. | |
| 0333137 | 9/1989 | European Pat. Off. | |
| 0511610 | 11/1992 | European Pat. Off. | |
| 0570850 | 11/1993 | European Pat. Off. | |
| 9316073 | 8/1993 | WIPO | 544/368 |
| 9418196 | 8/1994 | WIPO | |

*Primary Examiner*—Emily Bernhardt
*Attorney, Agent, or Firm*—Barbara E. Kurys

[57] ABSTRACT

This invention relates to compounds of the formula

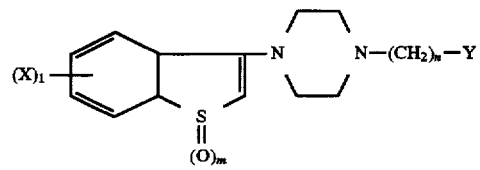

wherein

X is halogen, hydroxy, $(C_1-C_6)$alkoxy, amino or trifluoromethyl; and

Y is —CN or —$NR^1R^2$;
where l is an integer of 0, 1 or 2;

m is an integer of 0, 1 or 2;

n is an integer of 2, 3 or 4, except when Y is CN, in which case n can also be 1;

$R^1$ is hydrogen, $(C_1-C_6)$alkyl or $(C_1-C_6)$alkylcarbonyl;

$R^2$ is hydrogen, $(C_1-C_{10})$alkylcarbonyl, $(C_3-C_{12})$cycloalkylcarbonyl, hydroxy-$(C_1-C_6)$alkylcarbonyl, phenylcarbonyl, thienylcarbonyl or benzothienylcarbonyl;

or $R_1$ and $R^2$ together with nitrogen atom to which they are attached form the ring

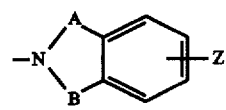

where A is C=O or $CH_2$; and B is C=O, CHOH, $CH_2$ or $CH_2CH_2$; and Z is halogen, hydroxy, $(C_1-C_6)$alkoxy, amino or trifluoromethyl p is 0 or 1; and pharmaceutically acceptable acid addition salts thereof, pharmaceutical compositions thereof and their use for the treatment of psychoses.

23 Claims, No Drawings

SUBSTITUTED BENZOTHIENYLPIPERAZINES AND THEIR USE

This is a continuation, of application Ser. No. 08/413,818, filed Mar. 17, 1995, now abandoned, which is herein incorporated by reference.

This invention relates to benzothienylpiperazines. More particularly, this invention relates to benzothienylpiperazines having antipsychotic activity and to their use as antipsychotic drugs.

The therapeutic treatment of schizophrenic patients by the administration of neuroleptic drugs, such as chlorpromazine, haloperidol, sulpiride, and chemically closely related compounds, is known in the art. Although control of schizophrenic symptoms has been successful, treatment with these drugs does not cure the psychotic patient, who will almost certainly relapse if medication is discontinued. Thus, there exists a continuing need in the art for antipsychotic drugs for the treatment of psychoses.

Moreover, some of the known neuroleptics produce unwanted side effects. For example, the side effects of many antipsychotic drugs include the so-called extrapyramidal symptoms, such as rigidity and tremor, continuous restless walking, and tardive dyskinesia which causes facial grimacing, and involuntary movements of the face and extremities. Orthostatic hypotension is also common. Thus, there also exits a need in the art for antipsychotic drugs that produce fewer or less severe manifestations of these common side effects.

This invention aids in fulfilling these needs in the art by providing a compound of the formula

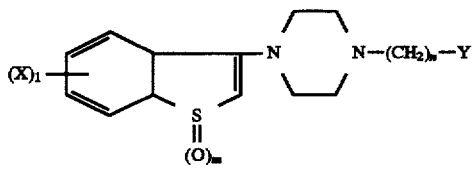

wherein

X is halogen, hydroxy, $(C_1-C_6)$alkoxy, amino or trifluoromethyl;

and

Y is —CN or —$NR^1R^2$;

where l is an integer of 0, 1 or 2;

m is an integer of 0, 1 or 2;

n is an integer of 2, 3 or 4, except where Y is CN, in which case n can also be 1;

$R^1$ is hydrogen, $(C_1-C_6)$alkyl or $(C_1-C_6)$alkylcarbonyl;

$R^2$ is hydrogen, $(C_1-C_{10})$alkylcarbonyl, $(C_3-C_{12})$cycloalkylcarbonyl, hydroxy- $(C_1-C_6)$alkylcarbonyl, phenylcarbonyl, thienylcarbonyl or benzothienylcarbonyl; or $R^1$ and $R^2$ together with nitrogen atom to which they are attached form the ring.

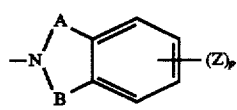

where

A is C =O or $CH_2$; and

B is C =O, CHOH, $CH_2$ or $CH_2CH_2$; and

Z is halogen, hydroxy, $(C_1-C_6)$alkoxy, amino or trifluoromethyl; p is 0 or 1 ; and pharmaceutically acceptable acid addition salts thereof, pharmaceutical compositions thereof and their use for the treatment of psychoses.

This invention also provides a pharmaceutical composition which comprises a compound of the invention and a pharmaceutically acceptable carrier. In one embodiment of the invention, the pharmaceutical composition is an antipsychotic composition comprising a compound of the invention in an amount sufficient to produce an antipsychotic effect.

In addition, this invention provides a method of treating psychoses, which comprises administering to a patient a pharmaceutically effective amount of a compound of the invention.

The compounds of this invention can contain a variety of different substituents and chemical groups.

The term "alkyl" as used herein refers to a straight or branched chain hydrocarbon group containing no unsaturation, such as, for example, methyl, ethyl, isopropyl, propyl, 2-butyl, t-butyl, neopentyl or hexyl.

The term "cycloalkyl" as used herein refers to monocyclic or bicyclic hydrocarbon ring such as, for example, cyclopropyl, cyclohexyl or adamantyl.

The term "alkoxy" as used herein refers to a monovalent substituent comprising an alkyl group linked through an ether oxygen having its free valence bond from the oxygen, such as, for example, methoxy, ethoxy, propoxy, butoxy, pentoxy or hexyloxy.

The term "alkylcarbonyl" as used herein refers to a monovalent substituent comprising an alkyl group linked through a carbonyl group, having its free valence bond from the carbonyl group, such as, for example, acetyl, propionyl or isopropylcarbonyl.

The term "phenyl" as used herein refers to unsubstituented phenyl or phenyl substituted with 1, 2 or 3 moieties selected from halogen, trifluoromethyl, phenyl, and $(C_1-C_6)$, alkyl such as, for example, 4-fluorophenyl and 2-(4-(trifluoromethyl)phenyl)-phenyl.

The term "thienyl" as used herein refers to unsubstituted thiophene, or thiophene substituted with 1 or 2 moieties selected from halogen, alkoxy, and $(C_1-C_6)$alkyl.

The term "benzothienyl" as used herein refers to unsubstituted benzothiophene or benzothiophene substituted with 1, 2 or 3 moieties in the benzo ring selected from halogen, trifluoromethyl, alkoxy and $(C_1-C_6)$alkyl.

Unless otherwise indicated, the term "halogen" as used herein refers to fluorine, chlorine, iodine and bromine.

Throughout the specification and appended claims, a given chemical formula or name shall encompass all geometric, optical and stereoisomers thereof where such isomers exit.

More particularly, this invention relates to a compound of the formula

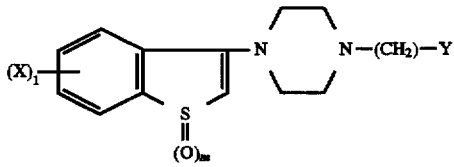

wherein

X is or halogen; and

Y is —CN or —$NR^1R^2$;

where m is an integer of 0 or 2;

n is an integer of 2, 3 or 4;

$R^1$ is hydrogen, $(C_1-C_6)$alkylcarbonyl;

$R^2$ is hydrogen, $(C_1-C_{10})$alkylcarbonyl, $(C_3-C_{12})$ cycloalkylcarbonyl, hydroxy-$(C_1-C_6)$alkylcarbonyl, phenylcarbonyl, thienylcarbonyl or benzothienylcarbonyl; or $R^1$ and $R^2$ together with nitrogen to which they are attached form the ring

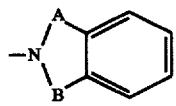

where

A is C=O or $CH_2$; and

B is C=O, CHOH, $CH_2$ or $CH_2CH_2$; and pharmaceutically acceptable acid addition salts thereof.

In one preferred embodiment of the invention are compounds of the formula

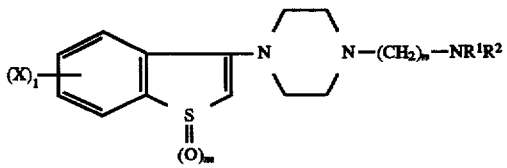

wherein

X is or halogen;

m is 0 or 2;

n is 2,3 or 4;

$R^1$ is hydrogen or $(C_1-C_6)$alkylcarbonyl; and $R^2$ is hydrogen, $(C_1-C_{10})$alkylcarbonyl, $(C_3-C_{12})$ cycloalkylcarbonyl, hydroxy$(C_1-C_6)$-alkylcarbonyl, thienylcarbonyl or benzothienylcarbonyl; and pharmaceutically acceptable acid addition salts.

Preferably in this embodiment

X is halogen;

m is 0; and n is 4.

Most preferably,

X is 6-F;

$R^1$ is hydrogen or acetyl; and $R^2$ is hydrogen, isopropylcarbonyl, adamantylcarbonyl, 4-fluorophenyl-carbonyl, 2-thienylcarbonyl, 2-benzothienylcarbonyl, 2-hydroxy-2-methylethylcarbonyl or 2-[4'-(trifluoromethyl)1,1'-biphenyl].

In another preferred embodiment of the invention are compounds of the formula

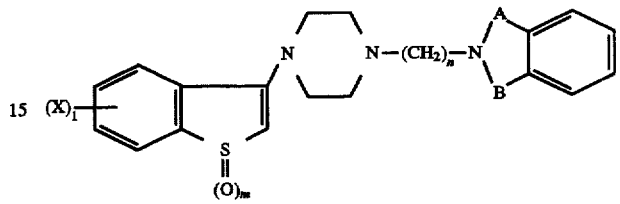

wherein

X is or halogen;

m is 0 or 2;

n is 2,3 or 4;

A is C=O or $CH_2$;

B is C=O, CHOH, $CH_2$ or $CH_2CH_2$; and its pharmaceutically acceptable acid addition salts.

Preferably, in this embodiment

X is halogen;

m is 0; and n is 4.

Most preferably, in this embodiment

X is 6-F;

m is 0;

n is 4;

A is C=O or $CH_2$; and

B is C=O, CHOH, $CH_2CH_2$ or $CH_2$.

The compounds of the invention are prepared in the following manner. The substituents $R^1$, $R^2$, A, B, X, Y and Z and the integers l, m and n are as defined above unless indicated otherwise.

The compounds of the invention are prepared by first reacting a suitably substituted 1-(benzo[b]thien-3-yl)-piperazine (A) with an appropriate haloalkylphthalimide (B) to obtain the compound of Formula II.

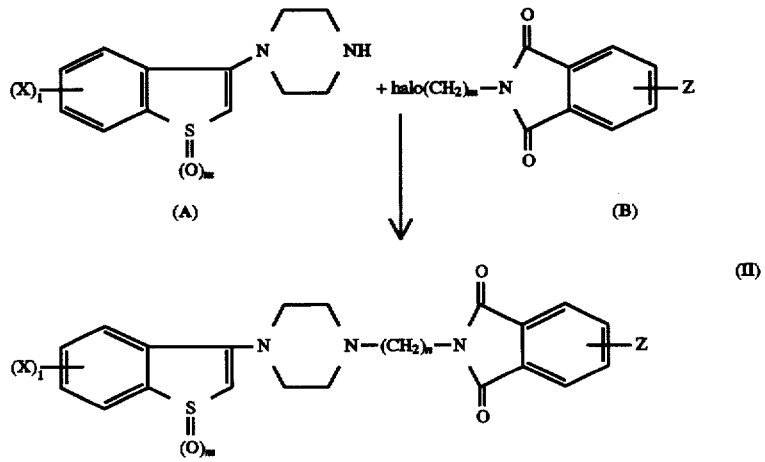

The reaction is typically carried out in a suitable solvent such as acetonitrile or dimethylformamide (DMF) in the presence of an acid scavenger such as, for example, potassium carbamate or sodium carbonate, and a small amount of potassium iodide or sodium iodide at temperatures of from about 20° C. to about 100° C., preferably from about

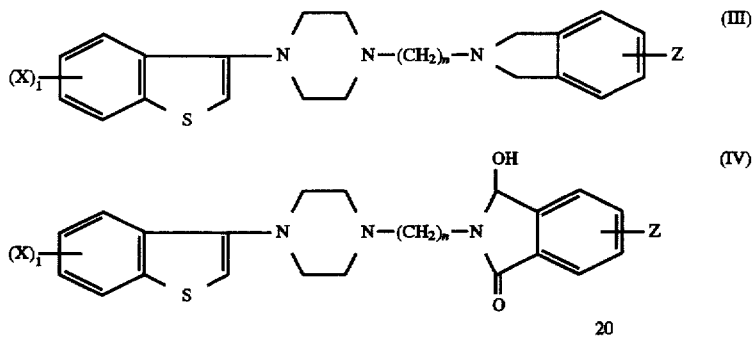

The compound of Formula IV is further reduced using a trialkylsilane such as triethylsilane and an organic carboxylic acid such as trifluoroacetic acid to give the lactam of Formula V.

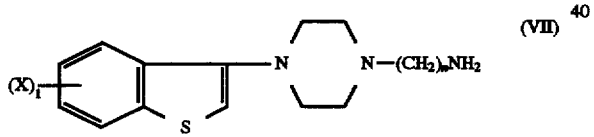

Typically, the reaction is carried out in an organic solvent such as dichloromethane at a temperature of from about 0° C. to about 25° C.

Alternatively, the compound of Formula II can be treated successively with sodium borohydride and acetic acid to provide the primary amine of Formula VII.

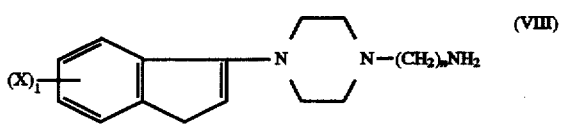

The reaction is typically carried out in an alcohol and water, preferably 6:1 isopropanol/water at a temperature of from about 20° C. to about 80° C.

The compound of Formula VII is reacted with an organic acid chloride to give a compound of Formula VIII.

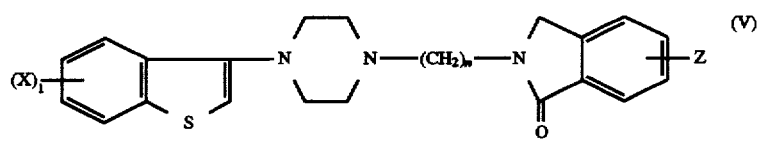

where $R^2$ is as defined above.

The reaction is typically carried out in a nonprotic organic solvent such as dichloromethane in the presence of an acid scavenger such as a tertiary amine, for example, triethylamine, at a temperature of from about 0° C. to about 30° C., preferably about 20° C.

The compound of Formula VIII is further acylated with a different organic acid chloride under the conditions described above to yield a compound of Formula I wherein $R^1$ is not hydrogen.

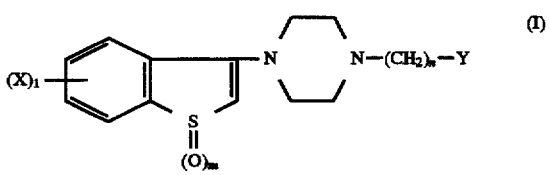

The sulfoxides and sulfones of the invention are prepared from the compounds of Formula I where m=0 or by means known in the art, for example, as disclosed in U.S. Pat. No. 5,240,927.

The starting compounds of Formula A are known in the art, for example, preps and lit refs. are covered in U.S. Pat. No. 5,240,927 and the references cited therein.

The compounds of the present invention are useful for treating psychoses by virtue of their ability to elicit an antipsychotic response in mammals. Antipsychotic activity is determined in the climbing mice assay by a method similar to those described by P. Protais, et al., Psychopharmacol., 50:1 (1976) and B. Costall, Eur. J. Pharmacol., 50:39 (1978).

Subject CK-1 male mice (23–27 grams) are group-housed under standard laboratory conditions. The mice are individually placed in wire mesh stick cages (4"×10") and are allowed one hour for adaption and exploration of the new environment. Then apomorphine is injected subcutaneously at 1.5 mg/kg, a dose causing climbing in all subjects for 30 minutes. Compounds to be tested for antipsychotic activity are injected intraperitioneally or given by oral doses at various time intervals., e.g. 30 minutes, 60 minutes, etc., prior to the apomorphine challenge at a screening dose of 10–60 mg/kg.

For evaluation of climbing, 3 readings are taken at 10, 20 and 30 minutes after apomorphine administration according to the following scale:

| CLIMBING BEHAVIOR MICE WITH: | SCORE |
|---|---|
| 4 paws on bottom (no climbing) | 0 |
| 2 paws on the wall (rearing) | 1 |
| 4 paws on the wall (full climb) | 2 |

Mice consistently climbing before the injection of apomorphine are discarded.

With full-developed apomorphine climbing, the animals are hanging on to the cage walls, rather motionless, over long periods of time. By contrast, climbs due to mere motor stimulation usually only last a few seconds.

The climbing scores are individually totaled (maximal score: 6 per mouse over 3 readings) and the total score of the control group (vehicle intraperitoneally-apomorphine subcutaneously) is set to 100%. The percent response at a dose of 20 mg/kg. or the $ED_{50}$ values with 95% confidence limits, calculated by a linear regression analysis, of some of the compounds of the present invention as well as a standard antipsychotic agent are presented in Table 1.

TABLE I

| ASSAY COMPOUND | CLIMBING MOUSE $ED_{50}$ mg/kg, ip @ 30 or % $t_{20}$ 20 ip @ 30 |
|---|---|
| N-[2-[4-(6-Fluorobenzo[b]thien-3-yl)-1-piperazinyl]-ethyl]-phthalimide | −25% |
| 2-[2-[4-(6-Fluorobenzo[b]thien-3-yl)-1-piperazinyl]-ethyl-2,3-dihydro-3-hydroxy-1H-isoindol-1-one | −43% @ 20 IP @ 30 |
| 2-[4-[4-(6-Fluorobenzo[b]thien-3-yl)-1-piperazinyl]butyl]-1H-isoindole-1,3(2H)-dione | −100% |
| N-[4-[4-(6-fluorobenzo[b]thien-3-yl)-1-piperazinyl]butyl-acetamide | 1.35 (1.1–1.67) MPK, IP @ 30 |
| N-Acetyl-N-[4-[4-(6-fluorobenzo[b]thien-yl)-1-piperazinyl]butyl]-2-methyl-propanamide | −75% @ 20 ip @ 30 |
| 4-(6-Fluorobenzo[b]thien-3-yl)-1-piperazinebutanamine(Z)-2-butenedioate | −34% @ 20 mpk, ip |
| N-[4-[4-(6-fluorobenzo[b]thien-3-yl)-1-piperazinyl]-butyl]-2-methyl-propanamide | 1.3 mg/kg, ip. |
| N-[4-[4-(6-Fluorobenzo[b]thien-3-yl)-1-piperazinyl]butyl]-adamantane-1-carboxamide maleate | −79 @ 20 mg/kg, ip. |
| N-[4-[4-(6-Fluorobenzo[b]thien-3-yl)-1-piperazinyl]butyl]-2-thiohene-carboxamide(Z)-2-butenedioate (1:1) | −100% @ 20 mg/kg, ip. |
| 4-(6-Fluorobenzo[b]thien-3-yl)-1-[4-(isoindol-2-yl)butyl]piperazine(Z)-2-butenedioate (1:2) | −33% @ 20 mg/kg, ip. |
| Sulpiride | 14.5 mg/kg ip |

Antipsychotic response is achieved when the compounds of the present invention are administered to a subject requiring such treatment as an effective oral, parenteral, or intravenous dose of from 0.01 to 50 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

Effective amounts of the compounds of the present invention can be administered to a subject by any one of several methods, for example, orally as in capsules or tablets, parenterally in the form of sterile solutions or suspensions, and in some cases intravenously in the form of sterile solutions.

The compounds of the present invention, while effective themselves, can be formulated and administered in the form of their pharmaceutically acceptable addition salts for purposes of stability, convenience of crystallization, increased solubility, and the like. Preferred pharmaceutically acceptable addition salts include salts of mineral acids, for example, hydrochloric acid, sulfuric acid, nitric acid, and the like, as well as organic acids such as salts of dibasic carboxylic acids, for example, maleic acid, fumaric acid, and salts of tribasic carboxylic acids, such as carboxysuccinic acid, citric acid, and the like.

Effective quantities of the compounds of the invention can be administered orally, for example, with an inert diluent or with an edible carrier. They can be enclosed in gelatin capsules or compressed into tablets. For the purposes of oral therapeutic administration, compounds of the invention can be incorporated with an excipient and used in the form of tablets, troches, capsules, elixirs, suspensions, syrups, wafers, chewing gums, and the like. These preparations should contain at least 0.5% of active compounds of the invention.

Tablets, pills, capsules, troches, and the like can also contain the following ingredients: a binder, such as microcrystalline cellulose, gum tragacanth or gelatin; an excipient, such as starch or lactose; a disintegrating agent such as alginic acid, Primogel, corn starch, and the like; a lubricant such as magnesium stearate or Sterotes; a glidant such as colloidal silicon dioxide; and a sweetening agent such as sucrose; or saccharin, or a flavoring agent, such as peppermint, methyl salicylate, or orange flavoring. When the dosage unit form is a capsule, it can contain, in addition to materials of the above type, a liquid carrier such as a fatty oil. Other dosage unit forms can contain various materials that modify the physical form of the dosage unit, for example, as coatings. Thus, tablets or pills can be coated with sugar, shellac, or other enteric coating agents. A syrup can contain, in addition to the active compounds, sucrose as a sweetening agent and certain preservatives, dyes, colorings and flavors. Materials used in preparing these various compositions should be pharmaceutically pure and non-toxic in the amounts used.

For the purpose of parenteral therapeutic administration, the active compound of the invention can be incorporated into a solution or suspension. These preparations should contain at least 0.1% of active compound, but can be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

Solutions or suspensions can also include the following components: a sterile diluent, such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates, and agents for the adjustment of tonicity such as sodium chloride or dextrose. The parenteral preparation can be enclosed in ampules, disposable syringes, or multiple dose vials made of glass or plastic.

The following examples are for illustrative purposes only and are not to be construed as limiting the invention. All temperatures are given in degrees Centigrade (° C.) unless indicated otherwise.

TABLE 2

| EX. No. | X | m | n | R¹ | R² | HZ |
|---|---|---|---|---|---|---|
| 1. | 6-Cl | 2 | 0 | — | — | — |
| 5. | 6-F | 0 | 4 | H | H | — |
| 6. | 6-F | 0 | 4 | H |  COCH₃ | — |
| 7. | 6-F | 0 | 4 |  COCH₃ |  COCH(CH₃)₂ | — |
| 8. | 6-F | 0 | 4 | 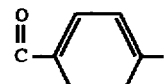 COCH(CH₃)₂ | H | — |
| 9. | 6-Cl | 0 | 0 | — | — | HCl |
| 10. | 6-F | 0 | 4 | H | 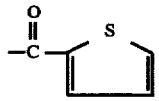 | — |
| 12. | 6-F | 0 | 4 | H |  | C₄H₄O₄ |
| 13. | 6-F | 0 | 4 | H | 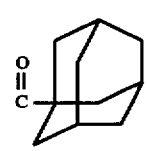 | C₄H₄O₄ |
| 16. | 6-F | 0 | 4 | H |  CC(CH₃)₂OH | — |
| 17. | 6-F | 0 | 4 | H |  | C₄H₄O₄ |
| 18. | 6-F | 0 | 4 | H | 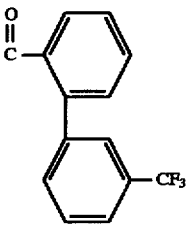 | C₄H₄O₄ |

TABLE 3

| EX. No. | X | m | n | Y | HZ |
|---|---|---|---|---|---|
| 2 | 6-F | 0 | 2 | 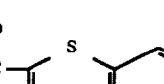 | — |
| 3 | 6-F | 0 | 2 |  | — |
| 4 | 6-F | 0 | 4 | 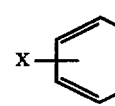 | — |
| 11 | 6-F | 0 | 4 | 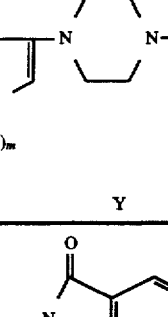 | — |
| 14 | 6-F | 0 | 3 | C≡N | C₄H₄O₄ |
| 15 | 6-F | 0 | 4 | 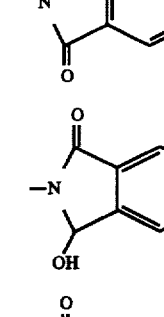 | 2 C₄H₄O₄ |

EXAMPLE 1

6-Chloro-3-piperazinylbenzo[b]thiophene-1,1-dioxide

A mixture of 3,6-dichlorobenzo[b]thiophene-1,1-dioxide (16.00 g, 0.0681 mol), piperazine (20.52 g, 0.238 mol) and dichloromethane (300 ml) was heated to reflux. After 1 hour, TLC analysis showed the dichlorosulfone ($R_f$=0.47, 30% ethyl acetate in hexanes, silica gel) to be consumed. The cloudy mixture was washed with 0.25 N NaOH (400 ml), H₂O (300 ml), brine (250 ml), dried (Na₂SO₄), and the solvent removed under reduced pressure. The residue was chromatographed on silica gel, eluting with 50% methanol in dichloromethane, to afford 12.90 g (66.5%) of a yellow solid. A 1.60 g sample was recrystallized from dichloromethane/ether yielding 0.480 g of light yellow crystals: m.p. 154° C. dec.

ANALYSIS

| Calculated for $C_{12}H_{13}ClN_2O_2S$: | 50.61% C | 4.60% H | 9.84% N |
|---|---|---|---|
| Found: | 50.43% C | 4.59% H | 9.73% N |

EXAMPLE 2

N-[2-[4-(6-Fluorobenzo[b]thien-3-yl)-1-piperazinyl]-ethyl]-phthalimide

A mixture of N-(2-bromoethyl)phthalimide (8.5 g, 33.55 mmol), (6-fluorobenzo[b]thien-3-yl)-1-piperazine (6.6 g, 27.96 mmol), $K_2CO_3$ (7.7 g, 55.8 mmol) and NaI (10 mg) in 150 ml dry $CH_3CN$ was heated to 85° with stirring under $N_2$. After 18 hours the mixture was cooled to room temperature, diluted with $H_2O$, and partitioned between $EtOAc/H_2O$. The organic phase was dried over $MgSO_4$, filtered and concentrated in vacuo. The residual orange solid was chromatographed on silica using 2:1 Heptane:EtOAc eluent to provide 11.30 g of crude product, (25.18 mmol, 90.07%) homogeneous by TLC (silica, 1:1 Heptane:EtOAc, $R_f$=0.20). This crude product was recrystallized from Heptane:EtOAc to provide as a first crop 3.92 g (9.58 mmol, 34.38%) of product as a white solid, m.p. 147–149, homogeneous by TLC.

ANALYSIS

| Calculated for $C_{22}H_{20}FN_3O_2S$: | 64.53% C | 4.92% H | 10.26% N |
|---|---|---|---|
| Found: | 64.39% C | 4.77% H | 10.25% N |

EXAMPLE 3

2-[2-[4-(6-Fluorobenzo[b]thien-3-yl)-1-piperazinyl]-ethyl-2,3-dihydro-3-hydroxy-1H-isoindol-1-one To a stirred suspension of N-[2-[4-(6-fluorobenzo[b]thien-3-yl)-1-piperazinyl]-ethyl]phthalimide (2.7 g, 6.6 mmol) in a mixture of 200 ml absolute EtOH and 50 ml $CH_2Cl_2$ under $N_2$ was added Sodium Borohydride (0.56 g, 14.8 mmol) in one portion. The mixture was stirred at room temperature for 15 minutes, during which time the solids dissolved. At the end of 15 minutes, TLC [silica, 1:1 heptane:EtOAc] showed no starting material remained and a major, lower $R_f$ spot had appeared.

The solution was concentrated in vacuo to a solid, which was filtered through a silica pad using EtOAc eluent. The filtrate was concentrated to a yellowish solid. This crude product was triturated with EtOAc, and the white solid obtained was collected and dried in vacuo. This provided a first crop of 1.56 g (3.79 mmol, 57.50%) of pure product, m.p. 188°–190°.

ANALYSIS

| Calculated for $C_{22}H_{22}FN_3O_2S$: | 64.21% C | 5.39% H | 10.21% N |
|---|---|---|---|
| Found: | 63.95% C | 5.19% H | 10.03% N |

EXAMPLE 4

2-[4-[4-(6-Fluorobenzo[b]thien-3-yl)-1-piperazinyl]butyl]-1H-isoindole-1,3(2H)-dione A mixture of 1-(6-fluorobenzo[b]thien-3-yl)-piperazine (20.0 g, 84.6 mmol), N-(4-bromobutyl)phthalimide (26.3 g, 93.2 mmol), anhydrous potassium carbonate (17.5 g, 127 mmol), KI (1.40 g, 8.43 mmol), and anhydrous acetonitrile (500 mL) was stirred at reflux for 17 hours. The thick slurry was filtered, the insolubles washed with chloroform (2×100 mL), and the filtrate concentrated in vacuo. The residue was taken up in chloroform (400 mL), washed with water (200 mL), and dried ($MgSO_4$). The solvent was removed in vacuo and the product chromatographed on silica gel, with 20% heptane/ethyl acetate as eluent, to afford 25.8 g of a yellow solid. Recrystallization from ether afforded 10.9 g (29%) of the title compound as a yellow powder: m.p.=94°–95° C.

ANALYSIS

| Calculated for $C_{24}H_{24}FN_3O_2S$: | 65.88% C | 5.53% H | 9.60% N |
|---|---|---|---|
| Found: | 65.82% C | 5.80% H | 9.54% N |

EXAMPLE 5

4-(6-Fluorobenzo[b]thien-3-yl)-1-piperazinebutanamine (Z)-2-butenedioate (1:2)

To a stirred mixture of 2-[4-[4-(6-fluorobenzo[b]thien-3-yl)-1-piperazinyl]-butyl]-1H-isoindole-1,3(2H)-dione (14.5 g, 33.1 mmol) and 6:1 isopropanol/water (170 mL) at room temperature and under a nitrogen atmosphere was added sodium borohydride (6.28 g, 166 mmol). After 25 hours acetic acid (35.7 g, 594 mmol) was carefully added. After stirring the mixture for 0.5 hours at room temperature the reaction was heated at 80° C. for 3 hours. The reaction mixture was concentrated in vacuo to a yellow residue which was dissolved in water (300 mL) and extracted with ether (150 mL). The aqueous layer was cooled to 0° C., basified with 50% aqueous NaOH to pH 12, and extracted with dichloromethane (2×125 mL). The combined extracts were washed with water (100 mL), dried ($K_2CO_3$), and concentrated in vacuo to afford 9.60 g of a sticky solid. Maleic acid (7.00 g, 60.3 mmol) was added to a solution of the impure free base (9.28 g, 30.2 mmol) in ethanol (300 mL) and the mixture heated until a solution was obtained. The solvent was removed in vacuo to give the crude salt as an orange-brown solid. After two recrystallizations from ethanol 9.82 g (55%) of the title compound was obtained as an off-white powder, m.p.=151°–153° C.

ANALYSIS

| Calculated for $C_{16}H_{22}FN_3S.C_8H_8O_8$: | 53.42% C | 5.60% H | 7.79% N |
|---|---|---|---|
| Found: | 53.72% C | 5.82% H | 7.74% N |

EXAMPLE 6

N-[4-[4-(6-Fluorobenzo[b]thien-3-yl)-1-piperazinyl]butyl-acetamide

To a 0° C. solution of 4-(6-fluorobenzo[b]thien-3-yl)-1-piperazine-butanamine (3.13 g, 10.2 mmol), triethylamine (1.45 g, 14.3 mmol), and dichloromethane (60 mL) under a nitrogen atmosphere was added acetyl chloride (0.883 g, 11.3 mmol) rapidly. The reaction was stirred at 0° C. for 2 hours and then at room temperature for an additional 1 hour. The reaction was diluted with dichloromethane (140 mL), washed with 5% aqueous NaOH (100 mL), and dried ($K_2CO_3$). The solvent was removed in vacuo to give a brown solid. The crude product was chromatographed on silica gel with 10% methanol/dichloromethane as eluent to afford a tan solid. Recrystallization from ethyl acetate gave 1.85 g (52%) of the title compound as beige crystals: m.p.=141°–142° C.

ANALYSIS

| Calculated For $C_{19}H_{24}FN_3OS$: | 61.86% C | 6.92% H | 12.02% N |
|---|---|---|---|
| Found: | 61.82% C | 7.01% H | 11.95% N |

EXAMPLE 7

N-Acetyl-N-[4-[4-(6-fluorobenzo[b]thien-3-yl)-1-piperazinyl]butyl]-2-methyl-propanamide A solution of isobutyryl chloride (2.34 g, 21.9 mmol) in dry dichloromethane (8 mL) was added over 2 minutes to a solution of N-[4-[4-(6-fluorobenzo[b]thien-3-yl)-1-piperazinyl]butyl]-acetamide (2.51 g, 7.18 mmol), triethylamine (2.18 g, 21.5 mmol), 4-dimethylaminopyridine (0.877 g, 7.18 mmol), and dry dichloromethane (50 mL) at room temperature under a nitrogen atmosphere. After 2.5 hours the reaction solution was diluted with dichloromethane (100 mL), washed with water (75 mL), dried over $MgSO_4$, and concentrated in vacuo. The residue was chromatographed on silica gel with 5% methanol/dichloromethane as eluent to give 2.91 g of an amber solid. Recrystallization from tert-butyl methyl ether/heptane afforded 1.52 g (50%) of the title compound as tan crystals: m.p.=98°–99° C.
ANALYSIS

| Calculated for $C_{22}H_{30}FN_3O_2S$: | 62.98% C | 7.21% H | 10.02% N |
|---|---|---|---|
| Found: | 63.20% C | 7.47% H | 10.05% N |

EXAMPLE 8

N-[4-[4-(6-fluorobenzo[b]thien-3-yl)-1-piperazinyl]butyl]-2-methyl-propanamide

To a 0° C. solution of 4-(6-fluorobenzo[b]thien-3-yl)-1-piperazine-butanamine (4.04 g, 13.1 mmol), triethylamine (1.89 g, 18.6 mmol), and dichloromethane (50 mL) under a nitrogen atmosphere was added isobutyryl chloride (1.63 g, 15.3 mmol) over 6 minutes. The reaction was stirred at 0° C. for 4 hours and then was diluted with dichloromethane (140 mL). The mixture was washed successively with 5% aqueous NaOH (100 mL) and water (100 mL), dried ($K_2CO_3$), and concentrated in vacuo to give an off-white solid. The crude product was chromatographed on silica gel with 10% methanol/dichloromethane as eluent to afford an off-white solid. Recrystallization from ethyl acetate/heptane gave 2.17 g (43%) of the title compound as beige needles: m.p. 130°–131° C. TLC (silica gel, 10% methanol/dichloromethane) $R_f$=0.37. The IR(CHCl_3), $^1$H NMR (CDCl_3, 200 MHz), and MS (M$^+$377, EI, 70 eV) were consistent for the assigned structure.
ANALYSIS

| Calculated for $C_{20}H_{28}FN_3OS$: | 63.63% C | 7.48% H | 11.13% N |
|---|---|---|---|
| Found: | 63.65% C | 7.59% H | 11.00% N |

EXAMPLE 9

1-(6-Chlorobenzo[b]thien-3-yl)-piperazine

To a mixture of 6-chloro-3-piperazinyl-benzo[b]thiophene-1,1-dioxide (6.0 g) and tetrahydrofuran (THF) (30 mL) under a nitrogen atmosphere was added a solution of DIBAL-H (diisobutylaluminum hydride) (0.084 mol) in toluene (84 mL) dropwise with ice bath cooling. The reaction mixture was stirred at 0° C. for 2 hours then overnight at room temperature. To the yellow solution was added, with vigorous stirring, water (5 ml) at a rate to control hydrogen evolution. Then 5NNaOH (5 mL) was added with rapid stirring. The resulting precipitate was filtered off and washed with dichloromethane and ether. The filtrate was concentrated in vacuo. The residue was taken up in dichloromethane (150 mL), washed with water (75 mml) and brine (100 ml), dried over sodium sulfate and concentrated in vacuo to yield 5.93 g of a viscous gummy material which was triturated with ether. The ether fraction was concentrated in vacuo to yield 2.75 g of residue which was chromatographed (silica gel, 50% MeOH/$CH_2Cl_2$) to yield 1.53 g product as a clear oil.

EXAMPLE 10

N-[4-[4-(6-Fluorobenzo[b]thien-3-yl)-1-piperazinyl]butyl]-4-fluoro-benzamide

To a 0° C. solution of 4-(6-fluorobenzo[b]thien-3-yl)-1-piperazine-butanamine (2.45 g, 7.97 mmol), triethylamine (1.23 g, 12.2 mmol), and dichloromethane (30 mL) under a nitrogen atmosphere was added 4-fluorobenzoyl chloride (1.61 g, 10.2 mmol) in one portion. The reaction was stirred at 0° C. for 70 minutes and then at room temperature for 3 hours. The reaction was diluted with dichloromethane (50 mL) and the mixture was washed successively with 5% aqueous NaOH (50 mL) and water (50 mL), dried ($Na_2SO_4$), and concentrated in vacuo to a tan solid. The crude product was chromatographed on silica gel with 10% ethanol/dichloromethane as eluent to afford an 2.22 g of an off-white solid. Recrystallization from ethyl acetate/heptane gave 1.60 g (46%) of the title compound as beige needles, m.p. 161°–163° C.
ANALYSIS

| Calculated for $C_{23}H_{25}F_2N_3OS$: | 64.32% C | 5.87% H | 9.78% N |
|---|---|---|---|
| Found: | 64.15% C | 5.68% H | 9.50% N |

EXAMPLE 11

4-(6-Fluorobenzo[b]thien-3-yl)-1-[4-(isoindol-2-yl)butyl]piperazine

To a stirred suspension of $LiAlH_4$ (1.50 g, 37.9 mmol) in anhydrous tetrahydrofuran (100 mL) under a nitrogen atmosphere at room temperature was added dropwise a solution of 2-[4-[4-(6-fluorobenzo[b]thien-3-yl)-1-piperazinyl]butyl]-1H-isoindole-1,3(2H)-dione (5.95 g, 13.6 mmol) in anhydrous tetrahydrofuran (125 mL) over 20 minutes. After the addition the reaction was stirred at 50° C. for 4 hours and then cooled to room temperature. The reaction was treated sequentially with water (1.5 mL), 15% NaOH (1.5 mL), and water (4.5 mL) and stirred at room temperature for 0.5 hours. The mixture was filtered, the insolubles washed with $CHCl_3$ (2 ×50 mL), and the filtrate concentrated in vacuo. The residue was dissolved in chloroform (200 mL), washed with water (100 mL), dried ($K_2CO_3$), and the solvent removed in vacuo. The crude product was chromatographed on silica gel with 10% methanol in dichloromethane as eluent to afford 3.50 g of a tan solid. The solid was recrystallized twice from ethyl acetate to afford 1.48 g (26%) of the title compound as amber crystals, m.p. 118°–120° C.

ANALYSIS

| Calculated for $C_{24}H_{28}FN_3S$: | 70.38% C | 6.89% H | 10.26% N |
|---|---|---|---|
| Found: | 70.52% C | 7.04% H | 10.18% N |

EXAMPLE 12

N-[4-[4-(6-Fluorobenzo[b]thien-3-yl)-1-piperazinyl]butyl]-adamantane-1-carboxamide maleate To a 0° C. solution of 4-(6-fluorobenzo[b]thien-3-yl)-1-piperazine-butanamine (2.50 g, 8.13 mmol), triethylamine (1.23 g, 12.2 mmol), and dichloromethane (50 mL) under a nitrogen atmosphere was added a solution of 1-adamantanecarbonyl chloride (2.00 g, 10.1 mmol) in dichloromethane (25 mL) rapidly. The reaction was stirred at 0° C. for 45 minutes and then at room temperature for 18 hours. The reaction solution was diluted with dichloromethane (75 mL) and was washed successively with 5% aqueous NaOH (75 mL) and water (75 mL), dried (Na$_2$SO$_4$), and concentrated in vacuo. The crude product was chromatographed on silica gel with 2–10% methanol/dichloromethane as eluent to afford 2.86 g of an off-white solid. To a solution of the free base (2.66 g, 5.66 mmol) in ethanol (60 mL) was added maleic acid (0.690 g, 5.94 mmol), the mixture heated until a solution was obtained, and the salt allowed to crystallize at room temperature. The salt was collected and recrystallized from methanol/ethyl acetate to afford 1.93 g (38%) of the title compound as an off-white powder, m.p. 200°–201° C. (dec.).

ANALYSIS

| Calculated for $C_{27}H_{36}FN_3OS \cdot C_4H_4O_4$: | 63.57% C | 6.88% H | 7.17% N |
|---|---|---|---|
| Found: | 63.36% C | 7.02% H | 7.12% N |

EXAMPLE 13

N-[4-[4-(6-Fluorobenzo[b]thien-3-yl)-1-piperazinyl]butyl]-2-thiophenecarboxamide (Z)-2-butenedioate (1:1)

To a 0° C. solution of 4-(6-fluorobenzo[b]thien-3-yl)-1-piperazine-butanamine (2.50 g, 8.13 mmol), triethylamine (1.23 g, 12.2 mmol), and dichloromethane (150 mL) under a nitrogen atmosphere was added 2-thiophenecarbonyl chloride (1.37 g, 9.34 mmol) in one portion. The reaction was stirred at 0° C. for 10 minutes and then at room temperature for 17 hours. The reaction was washed successively with 5% aqueous NaOH (75 mL) and water (75 mL), dried (Na$_2$SO$_4$), and concentrated in vacuo. The crude product was chromatographed on silica gel with 3 to 12% ethanol in chloroform as eluent to afford 2.66 g of a solid. To a solution of the freebase (2.50 g, 5.99 mmol) in ethanol (25 mL) was added maleic acid (0.730 g, 6.29 mmol), the mixture heated until a solution was obtained, and the solvent removed in vacuo. The salt was recrystallized from methanol/ethyl acetate to afford 2.35 g (54%) of the title compound as an off-white powder, m.p. 123°–126° C.

ANALYSIS

| Calculated for $C_{21}H_{24}FN_3OS_2 \cdot C_4H_4O_4$: | 56.27% C | 5.29% H | 7.87% N |
|---|---|---|---|
| Found: | 56.06% C | 5.48% H | 7.81% N |

EXAMPLE 14

4-(6-Fluorobenzo[b]thien-3-yl)-1-piperazinebutanenitrile (Z)-2-butenedioate (1:1)

A mixture of 1-(6-fluorobenzo[b]thien-3-yl)-piperazine (25.0 g, 0.106 mol), 4-bromobutyronitrile (18.8 g, 0.127 mol), anhydrous potassium carbonate (21.9 g, 0.158 mol), and anhydrous acetonitrile (250 mL) was stirred at reflux for 5.5 hours. The thick slurry was filtered, the insolubles washed with dichloromethane (2×50 mL), and the filtrate concentrated in vacuo. The residue was taken up in dichloromethane (300 mL), washed successively with 5% aqueous NaOH (150 mL) and water (150 mL), and dried (Na$_2$SO$_4$). The solvent was removed in vacuo and the crude product chromatographed on silica gel, with ethyl acetate as eluent, to afford 24.3 g (75%) of a yellow solid.

To a solution of the freebase (2.03 g, 6.69 mmol) in ethanol was added maleic acid (815 mg, 7.02 mmol) and the resulting mixture heated until a solution was obtained. After removal of the solvent in vacuo, the resulting salt was recrystallized from ethanol to yield 2.30 g of the title compound as off-white plates, m.p. 163°–165° C.

ANALYSIS

| Calculated for $C_{16}H_{18}FN_3S \cdot C_4H_4O_4$: | 57.27% C | 5.29% H | 10.02% N |
|---|---|---|---|
| Found: | 57.27% C | 5.19% H | 9.98% N |

EXAMPLE 15

4-(6-Fluorobenzo[b]thien-3-yl)1-[4-(isoindol-2-yl)butyl]piperazine (Z)-2-butenedioate (1:2)

To a 63° C. solution of 4-(6-fluorobenzo[b]thien-3-yl)-1-[4-(isoindol-2-yl)butyl]-piperazine (1.09 g, 2.66 mmol) in ethanol (40 mL) was added maleic acid (0.633 g, 5.45 mmol) and the resulting solution concentrated in vacuo to a dark foam. Trituration of the foam with ethanol/ethyl acetate gave a grey powder. The salt was treated with decolorizing charcoal in ethanol and recrystallized from ethanol to afford 1.08 g (63%) of the title compound as a grey powder, m.p. 153°–155° C.

ANALYSIS

| Calculated for $C_{24}H_{26}FN_3S \cdot 2C_4H_4O_4$: | 59.89% C | 5.65% H | 6.55% N |
|---|---|---|---|
| Found: | 59.80% C | 5.74% H | 6.53% N |

EXAMPLE 16

N-[4-[4-(6-Fluorobenzo[b]thien-3-yl)-1-piperazinyl]butyl]-2-hydroxy-2-methyl-propanamide (Z)-2-butenedioate (1:1)

To a solution of 2-hydroxyisobutyric acid (1.30 g, 12.5 mmol), pyridine (2.20 mL, 27.2 mmol), DMAP (190 mg, 1.56 mmol), and dichloromethane (60 mL) at ambient temperature under a nitrogen atmosphere was added chlorotrimethylsilane (3.40 mL, 26.8 mmol) dropwise over 3 minutes. After 4 hours the reaction was cooled at 0° C. and catalytic DMF (2 drops from a pasteur pipet) was added followed by oxalyl chloride (1.20 mL, 13.7 mmol) dropwise. The reaction was stirred at 0° C. for 1 hour and then at room temperature for 30 minutes. The reaction was cooled to 0° C. and a solution of 4-(6-fluorobenzo[b]thien-3-yl)-1-piperazinebutanamine (3.50 g, 11.4 mmol), pyridine (3.30 ml, 40.8 mmol) and dichloromethane (40 mL) was added in one portion. After 35 minutes at 0° C. the reaction mixture was stirred at room temperature for 18 hours. A solution of citric acid (4.60 g, 23.9 mmol) and methanol (50 mL) was added and the reaction stirred at room temperature for 50 minutes. After removal of the solvent in vacuo the residue was taken up in dichloromethane (125 mL), successively washed with 5% aqueous NaOH (100 mL) and water (100 mL), and dried ($K_2CO_3$). The solvent was removed in vacuo and the resulting brown liquid chromatographed on silica gel with 5% methanol in dichloromethane as eluent to afford 2.36 g of a gum.

The freebase (2.10 g, 5.34 mmol) was taken up in ethanol (50 ml), filtered, and maleic acid (650 mg, 5.60 mmol) was added to the filtrate. The resulting mixture was heated until a solution was obtained and the solvent removed in vacuo to give an orange solid. The salt was recrystallized repeatedly from methanol/ethyl acetate to yield 1.18 g (20%) of the title compound as off-white plates, m.p. 153°–155° C.

ANALYSIS

| Calculated for $C_{20}H_{28}FN_3S \cdot C_4H_4O_4$: | 56.57% C | 6.33% H | 8.25% N |
|---|---|---|---|
| Found: | 56.12% C | 6.30% H | 8.20% N |

EXAMPLE 17

N-[4-[4-(6-Fluorobenzo[b]thien-3-yl)-1-piperazinyl]butyl]-4'-(trifluoromethyl)-[1,1'-bilphenyl]-2-carboxamide (Z)-2-butenedioate (1:1)

To a mixture of 4'-(trifluoromethyl)-[1,1'-biphenyl]-2-carboxylic acid (2.60 g, 9.77 mmol), catalytic DMF, and anhydrous dichloromethane (30 mL) at room temperature under nitrogen was added oxalyl chloride (1.38 g, 10.9 mmol) dropwise over 15 minutes and the reaction stirred at room temperature. After 18 hours, the yellow reaction solution was concentrated in vacuo to give 2.51 g of 4'-(trifluoromethyl)-[1,1'-biphenyl]-2-carbonyl chloride as a cloudy yellow liquid which was used without further purification.

To a 0° C. solution of 4-(6-fluorobenzo[b]thien-3-yl)-1-piperazine-butanamine (2.50 g, 8.13 mmol), triethylamine (1.31 g, 12.9 mmol), and dichloromethane (75 mL) under a nitrogen atmosphere was added a solution of 4'-(trifluoromethyl)-1,1'-biphenyl]-2-carbonyl chloride (2.51 g, 8.82 mmol) and dichloromethane (25 mL) in one portion. The reaction was stirred at 0° C. for 0.5 hours and then at room temperature for 21.5 hours. The reaction was washed successively with 5% aqueous NaOH (75 mL) and water (75 mL), dried ($K_2CO_3$) and concentrated in vacuo. The crude product was chromatographed on silica gel with 5% ethanol in dichloromethane as eluent to afford 3.29 g of a product as a white foam.

To a solution of the freebase (2.99 g, 5.38 mmol) in ethanol (50 mL) was added maleic acid (0.656 g, 5.65 mmol), and the resulting solution concentrated in vacuo. The salt was recrystallized from ethyl acetate to afford 2.57 g (47%) of the title compound as a white powder, m.p. 158°–160° C.

ANALYSIS

| Calculated for $C_{30}H_{29}F_4N_3O \cdot C_4H_4O_4$: | 60.80% C | 4.95% H | 6.26% N |
|---|---|---|---|
| Found: | 60.52% C | 5.06% H | 6.15% N |

EXAMPLE 18

N-[4-[4-(6-Fluorobenzo[b]thien-3-yl)-1-piperazinyl]butyl]benzo[b]thiophene-2-carboxamide (Z)-2-butenedioate (1:1)

To a 0° C. solution of 4-(6-fluorobenzo[b]thien-3-yl)-1-piperazine-butanamine (2.50 g, 8.13 mmol), triethylamine (1.24 g, 12.2 mmol), and dry dichloromethane (100 mL) under a nitrogen atmosphere was added benzo[b]thiophene-2-carbonyl chloride (1.76 g, 8.95 mmol) dropwise over 15 minutes. Stirring was continued at 0° C. for 1.5 hours and at room temperature for 17.5 hours. The reaction was washed successively with 5% aqueous NaOH (75 mL) and water (75 mL), dried ($Na_2SO_4$), and concentrated dichloromethane as eluent to afford 3.34 g of a white solid.

To a solution of the freebase (3.08 g, 6.59 mmol) in boiling methanol (300 mL) was added maleic acid (800 g, 6.89 mmol) and the resulting solution was concentrated in vacuo to give a white solid. The salt was recrystallized from methanol/ethyl acetate to afford 3.07 g (64%) of the title compound as fine white crystals, m.p. 133°–135° C.

ANALYSIS

| Calculated for $C_{25}H_{26}FN_3OS_2 \cdot C_4H_4O_4$: | 59.67% C | 5.18% H | 7.20% N |
|---|---|---|---|
| Found: | 59.60% C | 5.13% H | 7.24% N |

It should be understood that this specification and examples are set forth by way of illustration and not limitation and that various modifications and changes may be made without departing from the spirit and scope of the present invention as defined by the appended claims.

We claim:

1. A compound of the formula

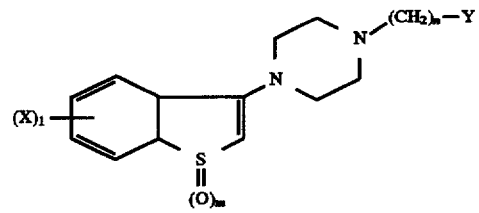

wherein

X is hydroxy, halogen, ($C_1$–$C_6$)alkoxy, amino or trifluoromethyl;

and

Y is —CN or $NR^1R^2$;

where l is an integer of 0, 1 or 2;

m is an integer of 0, 1 or 2;

n is an integer of 2, 3, or 4, except where Y is CN, in which case n can also be 1;

$R^1$ is hydrogen, ($C_1$–$C_6$)alkyl or ($C_1$–$C_6$)alkylcarbonyl; $R^2$ is hydrogen, ($C_1$–$C_{10}$)alkylcarbonyl, ($C_3$–$C_{12}$) cycloalkylcarbonyl, hydroxy($C_1$–$C_6$)alkylcarbonyl, substituted phenylcarbonyl, where the phenyl group is substituted with 1, 2, or 3 moieties selected from phenyl and 2(4'-trifluoromethyl)phenyl, thienylcarbonyl, substituted thienylcarbonyl where the thienyl group is substituted with 1 or 2 moieties selected from halogen, $(C_1-C_6)$alkoxy and $(C_1-C_6)$ alkyl, benzothienylcarbonyl or substituted benzothienylcarbonyl where the benzothienyl is substituted with 1, 2 or 3 moieties in the benzo ring selected from halogen, trifluoromethyl, $(C_1-C_6)$alkoxy and $(C_1-C_6)$ alkyl; with the proviso that when l is 0 and n is 4, $R^1$ and $R^2$ cannot both be hydrogen; or $R^1$ and $R^2$ together with the nitrogen atom to which they are attached form the ring

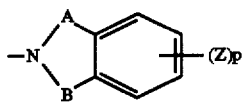

where

A is C=O or $CH_2$; and

B is CHOH, $CH_2$ or $CH_2CH_2$; and

Z is halogen, hydroxy, $(C_1-C_6)$alkoxy, amino or trifluoromethyl;

p is 0 or 1; or pharmaceutically acceptable acid addition salts thereof with the proviso that
when A is C=O, B is not $CH_2$, or $CH_2CH_2$.

2. The compound of claim 1 of the formula

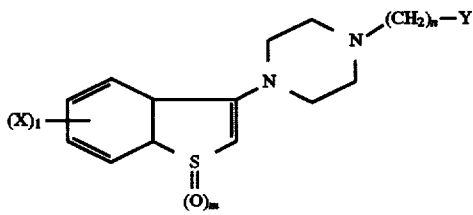

wherein

X is halogen;
and

Y is —CN or $NR^1R^2$;

where l is an integer of 0, 1 or 2;

m is an integer of 0 or 2;

n is an integer of 2, 3, or 4, except where Y is CN, in which case n can also be 1;

$R^1$ is hydrogen or $(C_1-C_6)$alkylcarbonyl;

$R^2$ is hydrogen, $(C_1-C_{10})$alkylcarbonyl, $(C_3-C_{12})$ cycloalkylcarbonyl, hydroxy$(C_1-C_6)$alkylcarbonyl, substituted phenylcarbonyl, where the phenyl group is substituted with 1, 2, or 3 moieties selected from phenyl and 2(4'-trifluoromethyl)phenyl, thienylcarbonyl, substituted thienylcarbonyl where the thienyl group is substituted with 1 or 2 moieties selected from halogen, $(C_1-C_6)$alkoxy and $(C_1-C_6)$ alkyl, benzothienylcarbonyl or substituted benzothienylcarbonyl where the benzothienyl is substituted with 1, 2 or 3 moieties in the benzo ring selected from halogen, trifluoromethyl, $(C_1-C_6)$alkoxy and $(C_1-C_6)$ alkyl; or $R^1$ and $R^2$ together with the nitrogen atom to which they are attached form the ring

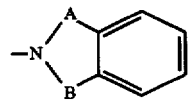

where

A is C=O or $CH_2$; and

B is CHOH, $CH_2$ or $CH_2CH_2$; or pharmaceutically acceptable acid addition salts thereof.

3. The compound of claim 2 of the formula

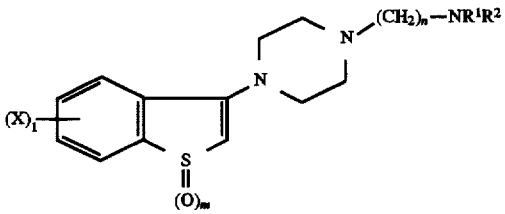

wherein

X is halogen;

l is 0, 1 or 2;

m is 0 or 2;

n is 2,3 or 4;

$R^1$ is hydrogen or $(C_1-C_6)$alkylcarbonl;

$R^2$ is hydrogen, $(C_1-C_{10})$alkylcarbonyl, $(C_3-C_{12})$ cycloalkylcarbonyl, hydroxy$(C_1-C_6)$alkylcarbonyl, thienylcarbonyl, substituted thienylcarbonyl where the thienyl group is substituted with 1 or 2 moieties selected from halogen, $(C_1-C_6)$alkoxy and $(C_1-C_6$ )alkyl, benzothienylcarbonyl or substituted benzothienylcarbonyl where the benzothienyl is substituted with 1, 2 or 3 moieties in the benzo ring selected from halogen, trifluoromethyl, $(C_1-C_6)$alkoxy and $(C_1-C_6)$ alkyl; or pharmaceutically acceptable acid addition salts thereof.

4. The compound of claim 3 wherein x is halogen;

m is 0; and n is 4.

5. The compound of claim 4 wherein

X is 6-F;

$R^1$ is hydrogen or acetyl; and $R^2$ is hydrogen, isopropylcarbonyl, adamantylcarbonyl, 2-thienylcarbonyl, 2-benzothienylcarbonyl, 2-hydroxy-2-methyl-ethylcarbonyl or 2-{4'-(trifluoromethyl)-1,1'-biphenyl }.

6. The compound of claim 5 which is 4-(6-fluorobenzo[b]thien-3-yl)-1-piperazinebutanamine (Z)-2-butene-dioate.

7. The compound of claim 5 which is N-[4-[4-(6-fluorobenzo[b]thien-3-yl)-1-piperazinyl]butyl-acetamide.

8. The compound of claim 5 which is N-acetyl-N-[4-[4-(6-fluorobenzo[b]thien-3-yl)-1-piperazinyl]butyl]-2-methyl-propanamide.

9. The compound of claim 5 which is N-[4-[4-(6-fluorobenzo[b]thien-3-yl)-1piperazinyl]butyl]-2-methyl-propanamide.

10. The compound of claim 5 which is N-[4-[4-(6-fluorobenzo[b]thien-3-yl)-1-piperazinyl]-butyl]-adamantane-1 -carboxamide maleate.

11. The compound of claim 5 which is N-[4-[4-(6-fluorobenzo[b]thien-3-yl)-1-piperazinyl]-butyl]-2-thiophenecarboxamide (Z)-2-butenedioate.

12. The compound of claim 5 which is N-[4-[4-(6-fluorobenzo[b]thien-3-yl)-1-piperazinyl]butyl]-2-hydroxy-2-methyl-propanamide (Z)-2-butenedioate.

13. The compound of claim 5 which is N-[4-[4-(6-fluorobenzo[b]thien-3-yl)-1-piperazinyl)butyl]-4'-(trifluoromethyl)-[1,1'-biphenyl]-2-carboxamide (Z)-2-butenedioate.

14. The compound of claim 5 which is N-[4-[4-(6-fluorobenzo[b]thien-3-yl)-1-piperazinyl]butyl]benzo[b]thiophene-2-carboxamide (Z)-2-butenedioate.

15. The compound of claim 2 of the formula

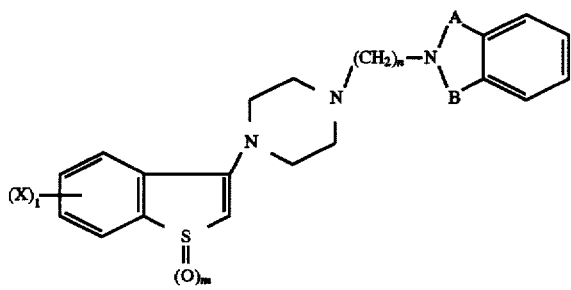

wherein
X is halogen;
l is 0, 1 or 2;
m is 0 or 2;
n is 2, 3, or 4;
A is C=O or CH$_2$; and
B is CHOH, CH$_2$ or CH$_2$CH$_2$;

or pharmaceutically acceptable acid addition salts thereof.

16. The compound of claim 15 wherein

X is halogen;

m is 0; and n is 4.

17. The compound of claim 16 wherein

X is 6-F;

m is 0;

n is 4;

A is C=O or CH$_2$; and

B is C=O, CHOH or CH$_2$.

18. The compound of claim 15 which is 2-[2-[4-(6-fluorobenzo[b]thien-3-yl)-1-piperazinyl]-ethyl-2,3-dihydro-3-hydroxy-1H-isoindol-1-one.

19. The compound of claim 15 which is 4-(6-fluorobenzo[b]thien-3-yl)-1-[4-(isoindol-2-yl)butyl]piperazine.

20. The compound of claim 2 which is 4-(6-fluorobenzo[b]thien-3-yl)-1-piperazinebutanenitrile (Z)-2-butenedioate.

21. The compound of claim 15 which is 4-(6-fluorobenzo[b]thien-3-yl)-1-[4-(isoindol-2-yl)butyl]piperazine (Z)-2-butenedioate.

22. A pharmaceutical composition which comprises a pharmaceutically acceptable carrier and a pharmaceutically effective amount of the compound of claim 1.

23. A method for treating psychoses which comprises administering to a patient in need thereof an antipsychotic effective amount of the compound of claim 1.

* * * * *